United States Patent [19]

Ward et al.

[11] Patent Number: 5,304,718
[45] Date of Patent: Apr. 19, 1994

[54] CYTOPLASMIC MALE STERILE QUINOA

[75] Inventors: Sarah M. Ward; Duane L. Johnson, both of Fort Collins, Colo.

[73] Assignee: Research Corporation Technologies, Inc., Tucson, Ariz.

[21] Appl. No.: 829,650

[22] Filed: Feb. 3, 1992

[51] Int. Cl.⁵ .................... A01H 5/00; A01H 5/10; A01H 1/00
[52] U.S. Cl. .................... 800/200; 800/255; 800/DIG. 9; 47/58
[58] Field of Search ............... 800/200, 255, DIG. 9; 47/58, 58.04

[56] References Cited

U.S. PATENT DOCUMENTS 4,672,035 6/1987 Davidonis et al. ............... 435/240

OTHER PUBLICATIONS

Allard, R. W. (1960) Principles of Plant Breeding, John Wiley and Sons, Inc., New York, pp. 234–251, 263–281.
Rea, J. (1969) *Turrialba 19:* 429–430.
Gandarillas, H. (1969) *Turrialba 19:* 429–430.
Risi, J. and N. W. Galwey (1984) *Adv. Applied Biology 10:* 145–216.
James, L. (1991) "Sarah Ward finds grain is ticket to degree and possibly new crop for U.S. agriculture" *Fort Collins Business World* Jun. 1991: 27–29.
Cusack, D. F. (1984) *Ecologist 14:* 21–31.
Simmonds, N. W. (1971) *Heredity 27:* 73–82.
Johnson and Croissant, "Alternative crop production and marketing in Colorado" *Colorado State University Technical Bulletin LTB90-3,* 1990.
Johnson and McCamant, "Quinoa research and development 1986" *Sierra Blanco Associates,* Denver Colo., 1988.
Burnouf-Radosevich and Paupardin (1985) *Amer. J. Bot. 72(2):* 278–283.
Johnson and Croissant, "Quinoa production in Colorado" *Service in Action* Colorado State University Cooperative Extension 112.
Risi, J. and N. W. Galwey (1991) "Effects of sowing date and sowing rate on plant development and grain yield of quinoa (*Chenopodium quinoa*) in a temperate environment" *Journal of Agricultural Science 1 117:325–332.*
Risi et al. (1984) "The Chenopodium Grains of the Andes" Inca Crops for Modern Agriculture *Adv. Applied Biology* 10:145–216.

*Primary Examiner*—David T. Fox
*Assistant Examiner*—E. F. McElwain
*Attorney, Agent, or Firm*—Scully, Scott, Murphy and Presser

[57] ABSTRACT

The present invention is directed to the use of a Apelawa variety of quinoa in the production of cytoplasmic male sterile quinoa plants and seeds useful in breeding programs for high-yield quinoa hybrids. More particularly, the present invention is directed to the use of cytoplasmic male sterile plants of the Apelawa variety of quinoa to produce plants and seeds for lines of quinoa varieties having male sterile cytoplasm; to cytoplasmic male sterile quinoa plants; quinoa seeds for cytoplasmic male sterile plants; and methods of producing cytoplasmic male sterile quinoa plants and seeds to create a source of cytoplasmic male sterile quinoa plants. A quinoa seed having male sterile cytoplasm and assigned ATCC accession no. 75154 is specifically disclosed.

13 Claims, No Drawings

CYTOPLASMIC MALE STERILE QUINOA

This invention was made with Government support under Hatch Act Funds awarded by the United States Department of Agriculture. The Government has certain rights in the invention.

FIELD OF THE INVENTION

Quinoa (*Chenopodium quinoa* Willd.) is a traditional Andean pseudocereal which is attracting increasing attention as an alternative dryland crop for areas of higher elevation and low precipitation. The present invention is directed to quinoa plants and seeds having male sterile cytoplasm derived from the Apelawa variety of quinoa; a method for producing cytoplasmic male sterile quinoa plants and seeds; the use of cytoplasmic male sterile plants of the Apelawa variety of quinoa to produce plants and seeds for additional lines of quinoa varieties having cytoplasm conferring the property of male sterility; and quinoa seeds to create a source of cytoplasmic male sterile quinoa plants. The cytoplasmic male sterile quinoa plants and seeds provided by the instant invention are useful in the breeding of high yield quinoa hybrids.

BACKGROUND OF THE INVENTION

Quinoa is classified as a member of the Chenopodiaceae, a large and varied family with world-wide distribution which also includes cultivated spinach and sugar beet. The genus Chenopodium contains over 120 species, mostly colonizing weedy annuals and is distinguished from the rest of the Chenopodiaceae by a five-parted perianth enclosing small, incomplete but perfect flowers and the smooth to roughened or honeycombed surface of the seeds. Wilson, H. D. (1990) (Chenopodium sect. Chenopodium subsect. Cellulata) *Econ. Bot.* 44(supp.): 92-110; Barklay, T. M., *Flora of the Great Plains* University Press of Kansas, Lawrence, Kans.; 1986. Important Chenopodium weed species include *C. album*, which is widely distributed in Europe, Asia and North America; *C. berlandieri*, found throughout the western United States, and *C. hircinum*, which is sympatric with quinoa throughout much of its South American range. Wilson, 1990; Wilson, H. D. (1980) *Syst. Bot.* 5(3): 253-263; Wilson, H. D. and C. B. Heiser (1979) *Amer. J. Bot.* 66: 198-206. The latter two species have the same chromosome number as quinoa (2n=36) and have been demonstrated to hybridize artificially with it. Wilson, H. D. (1988) *Syst. Bot.* 13: 215-228; Wilson, 1980; Wilson, H. D. (1976) "A biosystemic study of the cultivated chenopods and related species" Ph.D. diss. Indiana Univ., Bloomington, Ind.; Gandarillas, H. and J. Luizaga (1967) *Turrialba* 17: 275-279.

Quinoa is an extremely hardy and drought resistant plant which can be grown under harsh ecological conditions—high altitudes, relatively poor soils, low rainfall and cold temperatures—that other major cereal grains, such as corn and wheat, cannot tolerate. Cusack, D. F. (1984) *Ecologist* 14: 21-31.

Although the seed of quinoa is not a true grain, but a fruit, quinoa is referred to as a pseudocereal because of its unusual composition and balance of oil, protein and fat. Quinoa's protein content is approximately 13.8% which is from 2-6% above most wheats and an even higher percentage when compared to other cereals like barley, corn, and rice. In addition, quinoa has an exceptionally high level of lysine, which is not commonly found in the vegetable kingdom, as well as high levels of phosphorus, calcium, iron, Vitamin E and B-complex vitamins. Cusack, 1984; Cardozo, A. and M. Tapia, "Valor nutritivo" pp.149-192 in M. E. Tapia (ed.) *Quinoa y Kaniwa Cultivos Andinos* Serie Libros y Materials Educativos No. 49 Instituto Interamericano de Ciencias Agricolas, Bogota, Columbia, 1979. Consequently, quinoa provides an excellent source of nutrition for humans and animals. Although no single food can supply all of the essential nutrients, quinoa comes as close as any other in the vegetable or animal kingdom. Furthermore, since the value of quinoa proteins is believed to be at least equal to that of milk, quinoa holds exceptional promise as a weaning food for infants, especially in nutritionally-deficient third world areas. Cusack, 1984.

Quinoa can be used in food in a variety of ways such as to make cereal, to make soup, to make flour which can be used to make paste, cookies or, when combined with wheat flour, high protein breads, and to make drinks. Quinoa has a slightly sweet, nutty flavor and can be eaten alone like rice. The leaves of the quinoa plant can be eaten in salads. In addition, to its nutritional value and drought resistance, the key non-nutritional advantages of quinoa as a human food source are quinoa's palatability, easy preparation and versatility. Cusack, 1984; James, L. (1991) "Sarah Ward finds grain is ticket to degrees and possibly new crop for U.S. agriculture" *Fort Collins Business World* June, 1991: 27-29.

Quinoa plants can be bred by both self-pollination and cross-pollination techniques but are predominantly an inbreeding species. Plants usually bear hermaphrodite flowers which are self-fertile. Natural pollination occurs in quinoa when the wind blows pollen from one plant to another or from one flower on the same plant to another flower on the same plant, or, more uncommonly for quinoa, when pollen is transferred by insects.

With self-pollinating plants, hybrid plant breeding is more difficult since the plants of two different varieties can fertilize themselves as well as each other. Thus, the resulting progeny are a mixture of the hybrid and the two parental varieties. One method to avoid a mixture of progeny is to render nonfunctional the male properties of one parent One such technique to create male sterile plants, especially in self-pollinating plants, is emasculation. Emasculation techniques vary greatly, depending upon the size of the anthers, the position within the flower, and the relative time of maturity between the anthers and stigma. Manual emasculation involves removal of anthers (the male reproductive organ) from a plant and is labor intensive. See Welsh, J. R., *Fundamentals of Plant Genetics and Breeding*, John Wiley & Sons, Inc., 1981.

However, a more advantageous technique to render the male properties of a self-pollinating plant nonfunctional employs cytoplasmic male sterile plants. Cytoplasmic male sterility (cms) provides a reliable and inexpensive means to emasculate a plant for hybrid production.

Well-characterized male sterile systems have already been used to breed hybrids in a number of crop species, including maize, sugar beet and onion. The use of such a sterility system can be cost-effective and labor conscious. In corn, for instance, the expensive and laborious task of detasselling is avoided when cytoplasmic male sterility is utilized to avoid self-pollinating. The use of the cytoplasmic male sterile system in a breeding program is also advantageous because of its simplicity and economy.

Cytoplasmic male sterility, a maternally inherited trait, is most widely used in the hybrid industry to render the male properties of a plant nonfunctional. This type of sterility affects only pollen production; seed set is normal. Generally, all the progeny from a male sterile plant are themselves male sterile. However, in some cases male fertility can be restored Pearson, O. H. (1981) *Hort Sci.* 16: 482-487. Fertility can be restored either by cytoplasmic reversion to fertility or by a nuclear restorer gene able to override the effects of cytoplasm. MacKenzie, S. A. et al. (1988) *Proc. Natl. Acad. Sci. USA* 85: 2714-2717.

Typically, upon identification of a source of cytoplasmic male sterility, the trait is transferred to a desirable "female" or "A" line. A "maintenance" or "B" line lacking both the sterility trait and restoration factor is used to perpetuate and increase the female line. A "restorer" or "R" line, carrying a pollen fertility factor is used as a male to pollinate the cytoplasmic male sterile "A" line to create a hybrid variety. The cytoplasmic male sterile plant of the "A" line can be crossed with a plant from a different variety to produce hybrid progeny. This type of breeding program is often referred to as a cytoplasmic male sterile-restorer system.

Quinoa has value as a field crop, particularly, in highland areas (having cold dry climates) around the world which are currently limited as to crop diversity and the nutritional value of crops. The development of hybrid varieties is one method for increasing crop production. Thus, it is important to plant breeders to develop stable cytoplasmic male sterile quinoa lines for purposes of producing, high-yield quinoa hybrids that are agronomically sound. By doing so, the goals to maximize the amount of grain produced on the land used and to supply food for both animals and humans can be attained.

However, hybridization techniques involving manual emasculation and pollen transfer are extremely difficult to perform on quinoa plants, as well as time-consuming and expensive due to the small size of the quinoa flowers and the large number of flowers in each inflorescence. Thus, breeders have searched for cytoplasmic male sterile quinoa lines for the production of quinoa hybrids.

Male sterile quinoa plants have been reported. In the late 1960's the existence of a male sterile plant with empty anthers was reported; however, the stability and inheritance of the character was not investigated. Rea, J. (1969) *Turrialba* 19: 91-96. Furthermore, Rea notes the presence of empty anthers that varied in color from whitish-yellow to pale brown. The color of anthers in quinoa plants having a gene for male sterility have been observed to be a whitish-yellow. The anthers of normal fertile quinoa are generally bright lemon yellow.

In the late 1960's two male sterile quinoa lines derived from Bolivian material were described. These lines produced a male fertile $F_1$ generation when crossed with normal hermaphrodite pollen donors, and an $F_2$ generation which segregated in the ratio 3 male fertile: 1 male sterile. Gandarillas, H. (1969) *Turrialba*, 19: 429-430. This type of segregation was ascribed to a single nuclear recessive gene controlling male sterility, i.e., genic male sterility not stable cytoplasmic male sterility. A third male sterile line (Line 650 of the Quinoa Germplasm collection in the Patacamaya Experimental Station) which produced all male sterile offspring when crossed and backcrossed to five different male fertile pollen parents was also described. In that instance, the male sterile character of those plants was considered, but never fully established, to be under cytoplasmic control. Gandarillas, 1969.

In the early 1970's, an unstable nuclear-gene-generated cytoplasmic sterility in quinoa of Bolivian origin was reported. Simmonds, N. W., *Heredity* 27: 73-82, 1971. Further, Risi and Galwey describe work by Aguilar, who reported cytoplasmic male sterility in the quinoa line UNTA 292. This line appeared to produce male sterile progeny in the $F_1$ generation and on two successive backcrosses to male fertile pollen parents. Aguilar also reported that the cultivar Sajama apparently possesses a dominant nuclear gene which restores male fertility when combined with the cytoplasm of UNTA 292.

The development of male sterile quinoa lines to be used as the female parents in hybrid production has been suggested (Wilson, 1980; Risi, J. and N. W. Galwey (1984) *Adv. Applied Biology* 10: 145-216) but not yet reliably achieved. Hence, despite these potentially promising results, a reliable system of cytoplasmic male sterility in quinoa has not been reported, and cytoplasmic male sterile plants have not heretofor been available for commercial production of quinoa hybrids.

SUMMARY OF THE INVENTION

Accordingly, the present invention provides cytoplasmic male sterile quinoa plants of the Apelawa variety, seeds for cytoplasmic male sterile quinoa plants of the Apelawa variety, hybrid quinoa plants and seeds for hybrid quinoa plants. Apelawa quinoa seeds having male sterile cytoplasm, assigned ATCC accession no. 75154, are provided.

Another aspect of this invention is directed to a method for producing a source of cytoplasmic male sterile quinoa seeds by transferring male sterile cytoplasm from the quinoa variety Apelawa to another quinoa plant and thereby create a source of cytoplasmic male sterile quinoa plants.

In yet another aspect of this invention, a method is provided for producing seeds for cytoplasmic male sterile quinoa plants or seeds for cytoplasmic male sterile hybrid quinoa plants wherein cytoplasmic male sterile plants are used as the maternal parents.

In still another aspect of this invention, a method is provided for isolating cytoplasmic male sterile quinoa plants.

DETAILED DESCRIPTION OF THE INVENTION

The present invention relates to cytoplasmic male sterile quinoa plants that can be used, for example, in a breeding system to produce high-yielding quinoa hybrids. This invention provides cytoplasmic male sterile quinoa plants, seeds for cytoplasmic male sterile quinoa plants, hybrid quinoa plants, and seeds for hybrid quinoa plants. A method for producing hybrid quinoa plants and seeds for hybrid quinoa plants wherein cytoplasmic male sterile quinoa plants derived from the Apelawa variety are used as the maternal parent is also provided. Another aspect of this invention provides a method for producing a source of cytoplasmic male sterile quinoa plants and seeds.

In particular, the present invention provides quinoa plants and seeds having a stable cytoplasmic male sterile system. The cytoplasm conferring the property of male sterility is derived from the Apelawa variety of quinoa, and is referred to herein as "AP cytoplasm" or "male sterile cytoplasm".

Quinoa varieties have been categorized according to ecotype. There are five "ecotype varieties" of quinoa: valley, altiplano, saltflat, sealevel and subtropical. Risi and Galwey, 1984. The categorization of any particular population, land race, cultivar or variety of quinoa is dependent upon the adaptation of that variety to particular environmental conditions. As used herein, the term variety includes, but is not limited to, population, line, land race, cultivar and variety.

The Apelawa variety of quinoa, which originated in Bolivia, is an altiplano quinoa. Altiplano quinoa, grows at high altitudes (typically at 10,000 to 12,000 feet) in areas where frost is almost always a danger and where there is low rainfall. The altiplano plants themselves are characterized as more rapidly maturing, more cold tolerant, and more drought resistant than other types of quinoa. In addition, in comparison to other quinoa types, the altiplano seed heads are smaller and more compact. Risi and Galwey, 1984. As is typical of quinoas from the Lake Titicaca region, Apelawa shows a great deal of genetic variability. Similar to other altiplano quinoas, Apelawa plants are early maturing, unbranched, and approximately 4–5 feet in height at maturity. Apelawa inflorescences are compact and Apelawa's small seeds are brown, buff or pink in color. Apelawa leaves have clear indentations around the edges.

To produce the cytoplasmic male sterile quinoa plants of the present invention quinoa plants of the Apelawa variety having fewer than 40 seeds per plant are selected from a field. A plant that both self- and cross-pollinates typically bears fewer seeds if the male reproductive system is nonfunctional.

The seeds from the selected quinoa plants are then planted and cultivated in accordance with conditions and methodology known to one of ordinary skill in the art and, specifically, in accordance with the conditions set forth in Example 1. The planting and cultivating of quinoa are extensively detailed in Risi and Galwey, *Adv. Applied Biology* 10: 145–216, 1984; Johnson and Croissant, "Alternative crop production and Marketing in Colorado" *Colorado State University Technical Bulletin* LTB90-3, 1990; and Johnson and McCamant, "Quinoa research and development 1987" *Sierra Blanca Associates*, Denver, Colo., 1988; which are incorporated herein by reference.

The quinoa plants resulting from the cultivation of the seeds selected from the field of Apelawa plants are then visually examined for sterility. Plants are classified as male fertile, if anthers containing pollen grains are present, or male sterile, if anthers are absent or there is no visible pollen production. Plants classified as male sterile are crossed with fertile quinoa plants, for example, as set forth in Example 1 and, in accordance with the conditions and methodology known in the art. A cross can be obtained by placing the quinoa inflorescences in a bag, brushing the male fertile pollen on the cms quinoa plant or allowing natural cross-pollenation. See. e.g., Welsh, 1981. An extensive summary of crossing methods is described by W. R. Fehr and H. H. Hadley (eds.), *Hybridization of Crop Plants*, Am. Soc. Agron., Madison, Wis., 1980, incorporated herein by reference.

The seeds resulting from the crosses are collected, planted and cultivated as previously set forth. The resultant plants are again visually examined for characteristics of sterility. For a cytoplasmic male sterile plant, all of the progeny are male sterile, i.e., anthers are absent or there is no visible pollen production. Moreover, the progeny of another generation, produced as set forth above, are also male sterile. Apelawa seeds obtained from plants produced in accordance with this invention have been deposited with The American Type Culture Collection, 12301 Parklawn Drive, Rockville, Md. 20852, and assigned ATCC accession no. 75154. The deposited seeds are from quinoa plants of the Apelawa genotype having the Apelawa male sterile cytoplasm and have not been crossed with plants of any other variety.

Cytoplasmic male sterility (cms) is a maternally inherited trait In fertilization the female contributes a haploid nucleus and virtually all of the cytoplasm from the egg, while the male contributes a haploid nucleus but almost no cytoplasm from the pollen. The result being that the female cytoplasm which confers male sterility is passed from generation to generation. Information carried in the cytoplasm affecting the phenotype, i.e., anther presence or pollen production is contributed exclusively by the female. A specific cytoplasm can be carried along from generation to generation provided the plant possessing the cytoplasm is the maternal parent in each cross.

In accordance, with the present invention, the presence of Apelawa male sterile cytoplasm in a quinoa plant of any variety renders that particular plant's male reproductive system nonfunctional unless a gene restoring fertility or some otherwise unknown factor restoring fertility is also present. Accordingly, it is contemplated that any cytoplasmic male sterile plant derived from Apelawa cytoplasm constitutes a part of this invention. Thus, the AP cytoplasm can be transferred to and, therefore, be present in quinoa plants of any variety including, but not limited to, Apelawa, 407, Cahuil, Tango, Janco, Kanchi, Baer, Calcha, Chullpe, Killu-virginiana, Lihio, Marangani, Isluga, Sajama, Chuppi, Kanccolla, Blanca de Julí, Rosada de Junin, Blanca de Junín, Illimani, Oxfam, Tupiza, Ccoyto-1, Chewecca, Real, Pasankalla, Litû, Pichaman, Faro, Amarillo de Marangani Dulce de Quitopamba, Lipez, Lirio, Rojo de Cusco, and Tanso Kanta. The Apelawa cytoplasm capable of conferring the property of male sterility can also be transferred to quinoa plants cultivated from the quinoa seeds from the Universidad Nacional Techniadel Altiplano (UNTA) germplasm collection of quinoa, including, but not limited to, accession nos. 18, 39, 60, 63, 97, 98, 116 and 140.

The male sterile cytoplasm can be transferred from a quinoa plant of one variety to a quinoa plant of another variety. The method of transfer can be crossing the cytoplasmic male sterile quinoa plant with a fertile quinoa plant of the variety of quinoa plants to which the property of cytoplasmic male sterility is desired to be transferred. If necessary this cross can be followed by backcrossing to the male fertile parent. Any method of transfer known in the art can be used, for example, the methods set forth herein (e.g., backcrossing) or as substantially described in Simmonds, N. W., *Principles of Crop Improvement* Longman, N.Y. 1979, incorporated herein by reference.

Each part of a plant having AP cytoplasm is contemplated to be part of the present invention including roots, stems, leaves, and all flower parts. The cells of plants having AP cytoplasm can be grown in tissue culture which upon differentiation regenerate to form quinoa plants. Accordingly, these cells also form a part of this invention. Propagation of quinoa by shoot tip culture is described by Burnouf-Radosevich and Paupardin *Amer. J. Bot.* 72(2): 278-283, 1985, incorporated herein by reference.

Furthermore, it is contemplated that any plant, including, but not limited to, a hybrid quinoa plant containing the AP cytoplasm, constitutes a part of this invention. This includes, but is not limited to, the $F_1$ generation from a cross in which the maternal parent is a cytoplasmic male sterile (cms) quinoa plant.

In one embodiment, the present invention is directed to a method for producing a source of cytoplasmic male sterile quinoa plants which is characterized by the following steps:
  (a) identifying a quinoa plant having a male sterile cytoplasm; and
  (b) transferring said cytoplasm to a line of quinoa plants.

To produce a source of cytoplasmic male sterile plants, the technique used to identify the cytoplasmic male sterile quinoa plant can be, as substantially described above, by phenotypic selection for absence of anthers or absence of pollen production, or by any means known in the art. Although the initial quinoa plant having a trait for cytoplasmic male sterility is of the variety Apelawa, after the trait has been transferred in a manner, substantially as described above and known in the art, the quinoa plant identified that has the trait for cytoplasmic male sterility can be of any quinoa variety. The line of quinoa plants to which this trait is transferred can be of any quinoa variety since the male sterile cytoplasm originating in the Apelawa variety is stable.

As set forth in Example 1, transfers of the trait for cytoplasmic male sterility have been shown to be stable for two progeny generations. In a preferred embodiment, the male sterile cytoplasm is transferred by crossing the cms quinoa plant and a male fertile quinoa plant of the same or another variety of quinoa plants. By backcrossing the progeny of the cross to the fertile parent, the cms trait is transferred from generation to generation thereby perpetuating the line of cytoplasmic male sterile quinoa plants. After five or six backcrosses, if the male fertile parent is of a different quinoa variety than the male sterile parent, a new line of cytoplasmic male sterile quinoa plants has been created which essentially contains the genome of the male fertile plant ("working homozygosity").

One of the biggest advantages associated with the stability of the cytoplasmic male sterile system derived from the Apelawa is that the male sterile cytoplasm can be transferred from any quinoa variety having such cytoplasm. It is not necessary to start a line with a cytoplasmic male sterile Apelawa parent but a cms quinoa plant of any variety can be used and, therefore, the property of cytoplasmic male sterility can be transferred from generation to generation.

In another embodiment, the present invention is directed to a method for producing seed for a cytoplasmic male sterile quinoa plant characterized by the following steps:
  (a) growing a cytoplasmic male sterile quinoa plant;
  (b) pollinating said cytoplasmic male sterile quinoa plant with pollen from a male fertile quinoa plant; and
  (c) harvesting the seed developed on said cytoplasmic male sterile quinoa plant.

To produce a seed for a cytoplasmic male sterile quinoa plant, quinoa plants having AP cytoplasm, including but not limited to, plants of the variety Apelawa, can be grown or cultivated according to any conditions known to be suitable for quinoa plants or substantially as described herein. Such growth or cultivation can take place in a greenhouse under controlled conditions or in the field.

At maturity, upon anthesis, the cms plant is pollinated with pollen from a male fertile quinoa plant. Pollination can be effected by any method known to a skilled artisan including, but not limited to, placing the inflorescences in a bag, brushing the male fertile pollen on the cms quinoa plant or allowing natural cross pollination between the male sterile and male fertile quinoa plants. A number of methods of pollination are detailed in Welsh, J. R., *Fundamentals of Plant Genetics and Breeding*, John Wiley & Sons, Inc., 1981, incorporated by reference. These methods may be applied to the pollination of quinoa. The seeds developed on the cytoplasmic male sterile plants are small (approximately one-sixteenth of an inch in diameter) and can be harvested in accordance with conventional harvesting techniques and equipment. However, traditionally, the seeds are harvested by pulling or cutting the plants with a sickle and then leaving the plants in windrows to dry completely. The plants are then threshed either on a threshing floor with sticks, animals or vehicles, followed by winnowing, or else by using a stationary thresher. Risi and Galwey, pp.186-187, 1984.

Combines with regular grain heads (such as a John Deere 55, larger John Deeres and an International) or sorghum header attachments can be used to harvest the quinoa seeds. Due to the small size of the quinoa seed, adjustments to combines generally include reduction of air, reduction of cylinder speed, and use of smaller screens. Prior to combining, quinoa can be windrowed. If quinoa is picked up off the ground prior to combining the quinoa should be run through a destoner to remove small stones. Rain during harvests is undesirable since quinoa seed will germinate within 24 hours after exposure to moisture. When harvesting for human consumption all varieties of quinoa having saponin must be processed to remove the saponin. Such processing can be by washing with water, by using a grain polishing and debranning machine or by using a rice polisher. Incorporated by reference herein are the following references detailing quinoa harvesting techniques: Johnson and McCamant, 1988; Johnson and Croissant, 1990; and Johnson and Croissant, "Quinoa Production in Colorado" *Service in Action* Colorado State University Cooperative Extension 112. Of course, harvesting can also be done by hand.

The production of seeds for cytoplasmic male sterile quinoa hybrid plants is contemplated by the present embodiment. However, to produce a hybrid quinoa plant having cytoplasm conferring the trait of male sterility, the genotype of the male sterile parent and the genotype of the male fertile parent are different, i.e., the parents are from different varieties. For purposes of fertilizing a cms quinoa plant with pollen from a male fertile parent, due to the stability of the Apelawa derived cytoplasmic male sterile system, quinoa plants of any variety can be employed, including, but not limited to, the varieties previously described herein. Not only the first transfer of AP cytoplasm between two different varieties is contemplated to be within the present invention, but also any backcross or cross to a member of the $F_1$ progeny and further backcrosses or crosses to create a line (or new variety) of quinoa plants having working homozygosity with respect to genotype.

In still another embodiment, the present invention is directed to a method for producing seed for a cytoplasmic male sterile quinoa plant characterized by the following steps:
(a) planting in pollinating proximity a plant or seed for a cytoplasmic male sterile quinoa plant and a plant or seed for a male fertile quinoa plant;
(b) cultivating said plant or seed from said planting for a time and under conditions to produce said quinoa plants;
(c) allowing natural cross-pollination to occur between said quinoa plants; and
(d) harvesting seed produced on said cytoplasmic male sterile quinoa plants.

To produce seed for a cytoplasmic male sterile quinoa plant in the field, the task of manual pollination or fertilization is expensive and laborious. By planting the cms quinoa plants and the male fertile quinoa plants in pollinating proximity, manual pollination is unnecessary because the fertile plants will pollinate the cytoplasmic male sterile plants. The term "pollinating proximity" as used herein refers to the distance that two plants or two rows of plants can be planted from each other but can still cross-pollinate. With respect to quinoa, under average wind conditions, the two plants or rows of plants for which cross-pollination is desired, are planted no farther than 2 to 4 meters apart in distance and, for the maximum level of pollination, preferably, about 1 meter or less apart in distance to allow for natural cross-pollination. Typically, in the field, crop plants are planted in rows, thus, to achieve maximum cross-pollination in quinoa, alternating rows of cytoplasmic male sterile and male fertile quinoa plants should be preferably planted no farther than 0.5 meter apart.

To produce the seed of the present embodiment conventional methods of planting, cultivating and harvesting of quinoa plants can be used. In the present embodiment, the variety of the male sterile parent and the variety of the male fertile parent can be the same or different. Thus, it is contemplated that the present embodiment provides both seed for a quinoa plant having male sterile cytoplasm and seed for a hybrid quinoa plant having male sterile cytoplasm. Either plant used to produce the seed can be of any variety of quinoa, including, but not limited to the varieties previously set forth herein.

In yet another embodiment, the present invention provides a method for isolating cytoplasmic male sterile quinoa plants, i.e. growing cms quinoa plants in isolation. In the present embodiment seeds or plants of a cytoplasmic male sterile quinoa plant and seeds or plants of a male fertile quinoa plant are cultivated in pollinating proximity within a plot and that plot of plants is located at least 5 meters away from all other plants. By isolating the cytoplasmic male sterile quinoa plants and desired paternal parent, cross-pollination, or, in some cases, hybridization can be controlled. Only the plants within 5 meters of one another will cross-pollinate. For instance, alternating rows of cytoplasmic male sterile quinoa seeds and male fertile quinoa seeds can be planted approximately 1 meter apart and, preferably, less than 0.5 meters apart. To avoid cross-pollination or hybridization with plants not found within the plot, the closest plant, quinoa or otherwise, that should be planted or found growing within the plot should be at least 5 meters away in distance.

The present embodiment contemplates use of isolation techniques in the production of quinoa plants under natural field conditions, if necessary. Isolation techniques in the plant breeding context relate to methods that avoid the cross-pollination or hybridization of a particular plant with any plant(s) other than the desired mate. Such isolation methods can also be employed in greenhouses or under controlled conditions. Conventional methods of planting, cultivation and pollination of quinoa plants can be used. Due to the stability of the Apelawa derived cytoplasmic male sterile system, the type of plants used may be of any quinoa variety, including, but not limited to, the quinoa varieties previously set forth herein. Furthermore, the application of the present embodiment is not limited to the isolation of cytoplasmic male sterile quinoa plants, but can be applied in the production of any quinoa plant for which isolation is desired.

The cytoplasmic male sterile quinoa plants as well as quinoa seeds for producing cytoplasmic male sterile quinoa plants that are produced in accordance with any of the methods of the present invention can be utilized in cytoplasmic male sterile-restorer system hybrid breeding programs to produce new quinoa hybrid varieties and, in particular, new high yield quinoa hybrids.

A hybrid variety is the cross of two inbred lines, each of which may have one or more desirable characteristics either lacking by the other or complementing the other. $F_1$ is the designation given to the hybrid progeny of the first generation. Only $F_1$ hybrid plants and/or seeds are sought in the development of hybrids. The $F_1$ hybrid is more vigorous than its inbred parents. Increased yield is only one manifestation of hybrid vigor, or heterosis.

Since quinoa is a self-pollinating species, a cytoplasmic male sterile-restorer system is extremely valuable in the production of high yield quinoa hybrids. By crossing two quinoa varieties dissimilar in origin (i.e., Chilean×Bolivian) new hybrid varieties producing yields three times the average yield of 1344 kilograms per hectare can be produced.

To produce new high-yield quinoa hybrid varieties using a cytoplasmic male sterile-restorer system the development of 3 parent lines is required: a cytoplasmic male sterile "A" line, a maintenance "B" line lacking both the sterility property and a restoration factor, and an "R" line carrying a pollen fertility restorer. By using the methods for transferring AP cytoplasm of the present invention, cytoplasm capable of conferring the property of male sterility can be transferred to a line of quinoa plants intended to be the maternal parent in the new high-yield quinoa hybrid cross (the "A" line). The cytoplasmic male sterile plants of the "A" line and the male fertile plants of the "B" line can be of any quinoa variety. The "A" line is perpetuated by fertilization with pollen from a line of male fertile plants of the same variety (identical genotype) (the "B" line). The male fertile plants of the "B" line do not carry any factor, genic or otherwise, that restores fertility to the cms plants of the "A" line. To produce plants of the desired new high-yield quinoa hybrid variety, plants of the "A" line are crossed (or fertilized) with quinoa plants from the "R" line. "R" line quinoa plants are of a different variety than the plants of the "A" line and have the capacity to restore fertility to the "A" line cms quinoa plants. After harvesting, the seeds from the hybrid plant resulting from the cross can be commercially marketed and sold.

The seed of the cytoplasmic male sterile quinoa hybrid varieties, the hybrid quinoa plants produced from the seed, and various parts of the hybrid quinoa plant can be utilized, as previously described—namely, as a human and animal food source.

The following examples further illustrate the invention.

EXAMPLE 1

Thirty plants with poor seed set (fewer than 40 seeds per plant) were selected from a field population of the Bolivian quinoa variety Apelawa grown in the San Luis Valley (37° N latitude) in southern Colorado. Seed was removed from the dried panicles by hand and planted in a Colorado State University greenhouse in Fort Collins. The greenhouse temperature was maintained at 25° C. and plants were grown under natural daylength with no artificial illumination. Plants were raised in groups of 4 in 25 cm pots in commercial potting compost supplemented by a commercial liquid fertilizer. This resulted in plants 70 to 80 cm tall with an accelerated life cycle: flowering commenced 8 to 9 weeks after germination, with mature seeds at 14 weeks.

All plants were visually examined at flowering for the presence of anthers and the production of pollen. Plants in which anthers containing pollen grains were present in any flowers were classified as "male fertile". No attempt was made to ascertain viability of the pollen other than by selfing the plants. Plants without anthers or with no visible pollen production were classified as "male sterile". In the case of male sterile plants, a minimum of 10 flowers, selected at random from different parts of the inflorescence of each plant, was examined microscopically and the stage at which anther development aborted was recorded.

Male fertile plants were self-pollinated by enclosing the inflorescence in a waxed paper pollination bag during anthesis. Crossing of male sterile with male fertile pollen donors was achieved by enclosing both inflorescences in a single pollination bag for 7 to 10 days and shaking the bag each day to promote pollen transfer. Pollen donors were also selfed and 20 progeny from each donor plant were grown out to ensure that plants used as paternal parents were not heterozygous for recessive genic male sterility.

Twenty-nine of the 30 plants collected in the field yielded viable seed. Four progeny were raised from each of these plants, producing 29 $F_1$ families of unknown paternity. Each family was therefore presumed to be comprised of at least half-sibs. All male fertile plants in this generation were selfed, and the $F_2$ offspring raised and examined as described above. Male sterile plants in the $F_1$ generation were crossed, either to male fertile Apelawa pollen donors or to 407, a quinoa line of Chilean (Linares) origin which has undergone several cycles of selection for cultivation in Colorado. One male sterile plant (AP18-9) was crossed with a male fertile half-sib (AP18-12). In total, 23 crosses were made using male sterile plants as maternal parents in this generation. All male fertile progeny from these crosses were selfed. Four male sterile progeny from one cross (AP18-1×Apelawa) were backcrossed to Apelawa and four more male sterile progeny from the same cross were crossed with 407. Offspring from these crosses were again raised in the greenhouse as described above and examined at flowering.

Twenty-five of the 29 half-sib families raised consisted entirely of male fertile plants, but viable seed was obtained from only eight of these families when selfed. The remaining 17 male fertile families exhibited apparently normal pollen production, but selfing the plants produced either no seed or seed which subsequently failed to germinate. The $F_2$ generation from these 8 male fertile families consisted of 353 plants, all with normal hermaphrodite flowers and good seed set. The remaining four families consisted of a mixture of male sterile and male fertile plants. Re-examination of the original dried panicles collected from the field yielded additional viable seed in two cases. Total progeny numbers for the four segregating families in this generation are given in Table 1.

It was observed in the case of the male fertile plants that the number of flowers containing anthers in an individual inflorescence varied from over 90% to less than 10%, and that such flowers were always concentrated at the distal ends of the clusters. Anthers were completely absent throughout the entire inflorescence in all plants classified as male sterile. Microscopic examination of male sterile flowers revealed a ring of incomplete filaments surrounding the ovary, each filament with a threadlike extension replacing the anther at the distal end. Occasionally a double ring of such filaments was observed. On some male sterile plants the flowers lacked stamens entirely. Prominent exertion of stigmas was observed on the male sterile plants in all generations.

Only one male fertile plant (AP18-12) produced viable seed when selfed. This plant also produced offspring when used as the pollen donor in a cross with a male sterile half-sib (AP18-9). Progeny were obtained from 6 of the 22 other crosses using male sterile plants as maternal parents and either Apelawa or 407 as pollen donors. Details of crosses which resulted in progeny are given in Table 2.

As in Generation 1, the proportion of flowers containing anthers in the inflorescences of male fertile plants was observed to vary from 10% to over 90%, and flowers with anthers were concentrated at the distal ends of the clusters. All male fertile plants in this generation were selfed as described above, but no viable seed was obtained. Male sterile plants, as in Generation 1, were characterized by the complete absence of stamens, or by the presence of incomplete filaments with no anthers. Details of crosses made using (AP18-1×Apelawa) male sterile plants from Generation 2 as maternal parents are given in Table 3.

The successive transmission of male sterility through the female parent to produce two generations of all male sterile progeny indicates a cytoplasmically inherited trait. This form of male sterility is quite distinct from genic male sterility, both in the mode of transmission and in the stage at which pollen development is aborted.

TABLE 1

| Segregation in 4 half-sib families of Apelawa: Generation 1 | | |
|---|---|---|
| Family | Male fertile | Male sterile |
| AP12 | 2 | 2 |
| AP14 | 1 | 3 |
| AP18 | 4 | 10 |
| AP30 | 4 | 8 |

TABLE 2

Segregation in 2 families of Apelawa: Generation 2

| Female parent | Male parent | Progeny Male fertile | Male sterile |
|---|---|---|---|
| AP18-1 | Apelawa | 0 | 18 |
| AP18-5 | 407 | 0 | 39 |
| AP18-9 | AP18-12 | 15 | 16 |
| AP30-1 | Apelawa | 21 | 3 |
| AP30-7 | 407 | 0 | 39 |
| AP30-9 | 407 | 0 | 26 |
| AP30-12 | 407 | 0 | 37 |
| AP18-12 | Selfed | 24 | 1 |

TABLE 3

Segregation in Apelawa: Generation 3

| Female parent | Male parent | Progeny Male fertile | Male sterile |
|---|---|---|---|
| (AP18-1 × Apelawa) | 407 | 0 | 75 |
| (AP18-1 × Apelawa) | Apelawa | 0 | 78 |

EXAMPLE 2

Cytoplasmic male sterile plants derived from crosses of Example 1 between male sterile plants of the quinoa variety Apelawa and male fertile plants from the selection 407 were used as maternal parents. Normal male fertile plants of different South American quinoa varieties were used as pollen parents. Crossing of male sterile maternal parents with male fertile pollen donors was achieved by enclosing both inflorescences in a single waxed paper pollination bag for 7 to 10 days and shaking the bag each day to promote pollen transfer.

All plants were raised in a Colorado State University greenhouse in Fort Collins. Plants were grouped 4 to a 25 cm pot in commercial potting compost supplemented by a commercial liquid fertilizer. Greenhouse temperature was maintained at 25° C. and plants were grown under natural daylength with no artificial illumination. This resulted in plants 70 to 80 cm tall with an accelerated life cycle: flowering commenced 8 to 9 weeks after germination, with mature seed at 14 weeks. Seed for maternal parents and pollen donors was sown in late August and pollination was carried out in early November. Five crosses were made in total, each with a different pollen parent. Four full-sib cytoplasmic male sterile plants were used as maternal parents in each cross. Seed was harvested in December and planted to raise the $F_1$ hybrid generation in January; the $F_1$ progeny flowered in March and April and were backcrossed to the pollen parent in each case. All plants were visually examined at flowering for the presence of anthers and the production of pollen. In the case of male sterile plants, a minimum of 10 flowers, selected at random from different parts of the inflorescence of each plant, was examined microscopically and the stage at which anther development aborted was recorded.

A total of 92 $F_1$ plants, all male sterile, was obtained from the 5 crosses carried out. The flowers of the male sterile progeny resembled those of the maternal parents: anthers were completely absent, and a single (occasionally double) ring of filaments was present, each filament ending in a distal thread. Prominent exertion of stigmas was observed. Male sterile $F_1$ progeny in all crosses set seed readily when backcrossed to the pollen parent. Detailed results are given in Table 4.

TABLE 4

$F_1$ progeny from five crosses using cytoplasmic male steriles as maternal parents

| Female parent | Male parent | Progeny Male fertile | Male sterile |
|---|---|---|---|
| (AP30-7 × 407) | Cahuil | 0 | 19 |
| (AP18-5 × 407) | Tango | 0 | 27 |
| (AP30-9 × 407) | Janco | 0 | 21 |
| (AP18-5 × 407) | Kanchi | 0 | 6 |
| (AP30-12 × 407) | Baer | 0 | 19 |
| Totals | | 0 | 92 |

EXAMPLE 3

The methodology and materials of Examples 1 and 2 were used to produce additional quinoa varieties having male sterile cytoplasm. The male parents, were of the following quinoa varieties: Calche, Chullpe, Killu-virginiana, Lihio, Marangani, Isluga, Sajama and Chuppi. The maternal parent contained Apelawa male sterile cytoplasm. In each cross all of the $F_1$ progeny were observed to be cytoplasmic male sterile.

EXAMPLE 4

Ten rows of male sterile plants, having a genotype comprising 87% 407 and 13% Apelawa were planted in May 1991 at a site west of Fort Collins, at 7000 feet elevation. Each row had 35 plants. Temperatures were monitored during the growing season: The minimum recorded temperature was 36° F., the maximum recorded temperature was 88° F. The mean weekly high temperature was 82° F.; the mean weekly low temperature was 41° F. Every plant was visually examined at flowering for male sterility (i.e., absence of anthers) and 10 flowers were taken from a random sample of 20 plants for microscopic examination, to determine the actual floral structure. No anthers were seen on any of the male sterile plants, and the floral structure was exactly as seen in cytoplasmic male sterile plants grown in the greenhouse (stamens were either completely absent, or a ring of filaments was present, each ending in a thread instead of an anther).

EXAMPLE 5

In order to determine how far pollen travels under normal field growing condition red marker plants were used as pollen donors and green plants were used as pollen recipients since a red quinoa plant crossed with a green one will give red progeny. All plants used were normal fertiles (i.e., no cytoplasmic male steriles). Seeds were collected from green plants at measured distances from red plants and grown on the Colorado State University farm. Conventional methodology for planting, growing, cultivating and harvesting, as substantially described herein, was applied. Proportions of red and green progeny from each green plant tested were recorded.

The results can be summarized as follows:

| Distance from red pollen donor (cm) | % red progeny (i.e., level of outcrossing) |
|---|---|
| 33 | 1.3 |
| 40 | 0.62 |
| 78 | 0.52 |
| 100 | 0.84 |
| 200 | 0.12 |
| 300 | 0.0 |

| Distance from red pollen donor (cm) | % red progeny (i.e., level of outcrossing) |
|---|---|
| 400 | 0.13 |
| 500 | 0.0 |

The above results indicate a) that relatively little outcrossing occurs between normal quinoa plants, and b) that pollen movement over distances of more than 1 meter is negligible.

EXAMPLE 6

Since crop yield data for hybrid varieties of quinoa was not available nor previously reported, such an analysis was undertaken to establish that hybrid quinoa varieties produce higher crop yields relative to the parental varieties. Hybrid quinoa plants were produced by crossing fertile female quinoa lines having white or yellow panicle-types with male quinoa lines having red panicle-types. The crosses included emasculated (i.e., anthers removed manually) and nonemasculated lines for the female parent. Since the emasculated lines produced few seed, the seed obtained from the emasculated and nonemasculated female parents of the same variety was bulked prior to field planting.

The following lines of quinoa were used in the present example.

| Female parent (origin) | Male parent (origin) |
|---|---|
| Calcha (Bolivia) | Isluga red (S. Bolivia/N. Chile) |
| 407 (Chile) | 407-red (Chile) |
| Lipez (Chile) | Tanso Kanta (Peru) |
| Lirio (Chile) | Rojo de Cuzo (Peru) |
| | Chullpi (Chile) |
| | Calcha (Bolivia) |

Plots of 2m×3m were planted, cultivated and harvested in accordance with the methodology set forth herein. Plots were overseeded and thinned when red coloration of the male parent became apparent in the offspring. Non-red offspring were removed or left in place if spacing was greater than 15 cm between plants.

Table 5 identifies the average yield for each of the parental quinoa varieties used in the crosses of the present example. Table 6 shows increased yields for the hybrid varieties created by selective crossing of the parental varieties identified above.

TABLE 5

Average Yield for Selected Quinoa Varieties

| Variety | Yield (kg/ha) |
|---|---|
| 407 | 1206 |
| Lipez | 1076 |
| Isluga | 1074 |
| Lirio | 943 |
| Chullpi | 756 |
| Calcha | 435 |
| Tanso Kanta | 0 |
| Rojo de Cusco | 0 |

TABLE 6

Yields of Quinoa Hybrids

| Cross Female Parent × Male Parent | Yield (kg/ha) |
|---|---|
| 407 × Calcha - R | 5922 |
| Lipez × Calcha - R | 3744 |
| Lirio × 407 - R | 3126 |
| Lipez × 407 - R | 2922 |
| 407 × Tanso Kanta | 2616 |
| 407 × Chullpi - R | 1896 |
| 407 × Isluga - R | 1404 |
| Calcha × Rojo de Cusco | 876 |

This example thus demonstrates that hybrid varieties of quinoa produce higher crop yield relative to the parental varieties. Similar high yields are expected in crosses wherein the female parent in the crosses is cytoplasmic male sterile and the male parent contains a gene or other factor restoring fertility.

What is claimed is:

1. A quinoa seed of the variety Apelawa having male sterile cytoplasm and assigned ATCC accession no. 75154.

2. A quinoa plant produced from the quinoa seed of claim 1.

3. A cytoplasmic male sterile quinoa progeny plant of a quinoa plant having Apelawa male sterile cytoplasm wherein said progeny plant has Apelawa male sterile cytoplasm derived from a plant produced from a quinoa seed assigned ATCC accession no. 75154.

4. A quinoa seed produced from the cytoplasmic male sterile quinoa progeny plant of claim 3.

5. The progeny plant according to claim 3 wherein said progeny plant is produced by crossing a cytoplasmic male sterile quinoa plant having Apelawa male sterile cytoplasm and of any quinoa nuclear genome with a fertile quinoa plant of any quinoa nuclear genome.

6. A root, stem, leaf, or flower of the cytoplasmic male sterile quinoa progeny plant according to any one of claims 2 or 3.

7. A method for producing a cytoplasmic male sterile quinoa progeny plant comprising:
   (a) identifying a female designated quinoa plant having Apelawa male sterile cytoplasm wherein said Apelawa male sterile cytoplasm is derived from a plant produced from a quinoa seed assigned ATCC accession no. 75154; and
   (b) transferring said Apelawa male sterile cytoplasm to a progeny quinoa plant, wherein said transferring is by pollination;
   to produce a progeny plant which is a cytoplasmic male sterile quinoa plant.

8. The method according to claim 7 wherein said transferring in step (b) is by crossing said female designated quinoa plant having male sterile cytoplasm with a male designated fertile quinoa plant of said progeny quinoa plant to produce the cytoplasmic male sterile quinoa progeny plant.

9. The method according to claim 7 wherein said transferring is by backcrossing said female-designated quinoa plant with said progeny quinoa plant.

10. The method according to claim 7 wherein identifying in step (a) comprises selecting said quinoa plant having at least one of the following characteristics: lack of male reproductive organs, lack or stamens, or lack of anthers.

11. A hybrid quinoa plant having Apelawa male sterile cytoplasm wherein said Apelawa male sterile cytoplasm is derived from a female-designated cytoplasmic male sterile quinoa plant produced from a quinoa seed assigned ATCC accession no. 75154.

12. The hybrid quinoa plant according to claim 11 wherein said hybrid quinoa plant is produced by crossing a cytoplasmic male sterile quinoa plant, having Apelawa male sterile cytoplasm, of any quinoa nuclear genome with a fertile quinoa plant of any quinoa nuclear genome.

13. A hybrid quinoa seed having Apelawa male sterile cytoplasm wherein said Apelawa male sterile cytoplasm is derived from a female designated cytoplasmic male sterile quinoa plant produced from a quinoa seed assigned ATCC accession no. 75154.

* * * * *

UNITED STATES PATENT AND TRADEMARK OFFICE
CERTIFICATE OF CORRECTION

PATENT NO. : 5,304,718
DATED : April 19, 1994
INVENTOR(S) : Sarah M. Ward, et al.

It is certified that error appears in the above-indentified patent and that said Letters Patent is hereby corrected as shown below:

On the Title Page, Section [56], under "OTHER PUBLICATIONS", lines 5-6: delete "Risi, J. and W. Galwey (1984) Adv. Applied Biology 10: 145-216."

Column 2, line 18: "paste" should read --pasta--

Column 2, line 43: after "parent" insert --.--

Column 3, line 7: after "restored" insert --.--

Signed and Sealed this

Sixth Day of December, 1994

Attest:

BRUCE LEHMAN

Attesting Officer

Commissioner of Patents and Trademarks